US012788411B2

(12) United States Patent
Bono et al.

(10) Patent No.: US 12,788,411 B2
(45) **Date of Patent: *Nov. 10, 2026**

(54) ROTARY OSCILLATING BONE, CARTILAGE, AND DISK REMOVAL TOOL ASSEMBLY

(71) Applicant: GLOBUS MEDICAL, INC., Audubon, PA (US)

(72) Inventors: Peter L. Bono, Bingham Farms, MI (US); James D. Lark, King of Prussia, PA (US); Corey A. Freimark, Grand Haven, MI (US); Anthony J. Ruhala, Almont, MI (US)

(73) Assignee: Globus Medical, Inc., Audubon, PA (US)

( * ) Notice: Subject to any disclaimer, the term of this patent is extended or adjusted under 35 U.S.C. 154(b) by 71 days.

This patent is subject to a terminal disclaimer.

(21) Appl. No.: 18/923,125

(22) Filed: Oct. 22, 2024

(65) Prior Publication Data

US 2025/0040941 A1 Feb. 6, 2025

Related U.S. Application Data

(60) Continuation of application No. 17/842,296, filed on Jun. 16, 2022, now Pat. No. 12,137,919, which is a (Continued)

(51) Int. Cl.
*A61B 17/16* (2006.01)
*A61B 17/14* (2006.01)
(Continued)

(52) U.S. Cl.
CPC ...... *A61B 17/1624* (2013.01); *A61B 17/1671* (2013.01); *A61B 17/32002* (2013.01); (Continued)

(58) Field of Classification Search
CPC .................. A61B 17/14; A61B 17/148; A61B 17/320016; A61B 17/16; A61B 17/1622; A61B 17/1615; A61B 17/1624; A61B 17/1626; A61B 17/1628; A61B 17/8875; A61B 17/8897; B23B 51/00; Y10T 74/2107; Y10T 74/2101; Y10T 74/18568; Y10T 74/18056; Y10T 74/1518; (Continued)

(56) References Cited

U.S. PATENT DOCUMENTS 12,137,919 B2 * 11/2024 Bono ............... A61B 17/32002
2007/0282344 A1 * 12/2007 Yedlicka ............ A61B 17/1671 606/80

* cited by examiner

*Primary Examiner* — Marcela I. Shirsat

(57) ABSTRACT

A bone, cartilage, and disk removal tool assembly is provided with a motor mounted in a housing. A spindle is mounted for rotation to the housing. A rack-and-pinion mechanism is operably driven by the motor and connected to the spindle to oscillate the spindle for providing a rotary oscillating cutting operation. According to at least another embodiment, a plurality of cams is supported in the housing and driven for rotation by the motor. A plurality of followers is mounted for rotation to the housing, in engagement with the plurality of cams so that one rotation of the plurality of cams oscillates the plurality of followers more than once while preventing over-rotation of the plurality of followers. A peak angular acceleration of the spindle is less than nine million radians per second squared.

15 Claims, 16 Drawing Sheets

Related U.S. Application Data continuation of application No. 16/266,802, filed on Feb. 4, 2019, now Pat. No. 11,389,179, which is a division of application No. 13/469,665, filed on May 11, 2012, now Pat. No. 10,194,922.

(51) Int. Cl.
*A61B 17/32* (2006.01)
*A61B 17/88* (2006.01)

(52) U.S. Cl.
CPC ............ *A61B 17/14* (2013.01); *A61B 17/162* (2013.01); *A61B 17/1622* (2013.01); *A61B 17/1628* (2013.01); *A61B 17/320016* (2013.01); *A61B 2017/320028* (2013.01); *A61B 17/8875* (2013.01); *A61B 17/8897* (2013.01); *Y10T 74/1683* (2015.01); *Y10T 74/2101* (2015.01); *Y10T 74/2107* (2015.01)

(58) Field of Classification Search
CPC .......... Y10T 74/18528; Y10T 74/1683; Y10T 74/18024; Y10T 74/1526
USPC ..... 606/80; 408/124, 173; 74/70–83, 88–89, 74/99 R, 126, 133, 20–21, 25, 103, 9, 74/10.33, 10.35, 10.37, 10.6, 838, 53–56, 74/122, 124–125, 497, 567, 569
See application file for complete search history.

| Drive System | Motor Speed | | Oscillations Per Motor Revolution | Oscillations | Oscillation Range | | Oscillation Amplitude | | Peak Velocity | Peak Acceleration | Peak Jerk |
|---|---|---|---|---|---|---|---|---|---|---|---|
| | RPM | Rad/sec | | OPM | Degrees | Radians | Degrees | Radians | Rad/sec | Rad/sec2 | Rad/sec3 |
| Shuttle | 5000 | 523.6 | 1 | 5000 | 143.24 | 2.5 | 71.61972 | 1.25 | 6.54E+02 | 3.43E+05 | 1.79E+08 |
| | 10000 | 1047.2 | 1 | 10000 | 143.24 | 2.5 | 71.61972 | 1.25 | 1.31E+03 | 1.37E+06 | 1.44E+09 |
| | 15000 | 1570.8 | 1 | 15000 | 143.24 | 2.5 | 71.61972 | 1.25 | 1.96E+03 | 3.08E+06 | 4.84E+09 |
| | 20000 | 2094.4 | 1 | 20000 | 143.24 | 2.5 | 71.61972 | 1.25 | 2.62E+03 | 5.48E+06 | 1.15E+10 |
| | 25000 | 2618 | 1 | 25000 | 143.24 | 2.5 | 71.61972 | 1.25 | 3.27E+03 | 8.57E+06 | 2.24E+10 |
| | 30000 | 3141.6 | 1 | 30000 | 143.24 | 2.5 | 71.61972 | 1.25 | 3.93E+03 | 1.23E+07 | 3.88E+10 |
| | 35000 | 3665.2 | 1 | 35000 | 143.24 | 2.5 | 71.61972 | 1.25 | 4.58E+03 | 1.68E+07 | 6.15E+10 |
| | 40000 | 4188.8 | 1 | 40000 | 143.24 | 2.5 | 71.61972 | 1.25 | 5.24E+03 | 2.19E+07 | 9.19E+10 |
| Cam | 5000 | 523.6 | 2 | 10000 | 90 | 1.57 | 45 | 0.79 | 8.22E+02 | 8.61E+05 | 9.02E+08 |
| | 10000 | 1047.2 | 2 | 20000 | 90 | 1.57 | 45 | 0.79 | 1.64E+03 | 3.45E+06 | 7.22E+09 |
| | 15000 | 1570.8 | 2 | 30000 | 90 | 1.57 | 45 | 0.79 | 2.47E+03 | 7.75E+06 | 2.44E+10 |
| | 20000 | 2094.4 | 2 | 40000 | 90 | 1.57 | 45 | 0.79 | 3.29E+03 | 1.38E+07 | 5.77E+10 |
| | 25000 | 2618 | 2 | 50000 | 90 | 1.57 | 45 | 0.79 | 4.11E+03 | 2.15E+07 | 1.13E+11 |
| | 30000 | 3141.6 | 2 | 60000 | 90 | 1.57 | 45 | 0.79 | 4.93E+03 | 3.10E+07 | 1.95E+11 |
| | 35000 | 3665.2 | 2 | 70000 | 90 | 1.57 | 45 | 0.79 | 5.76E+03 | 4.22E+07 | 3.09E+11 |
| | 40000 | 4188.8 | 2 | 80000 | 90 | 1.57 | 45 | 0.79 | 6.58E+03 | 5.51E+07 | 4.62E+11 |

FIG. 24

ROTARY OSCILLATING BONE, CARTILAGE, AND DISK REMOVAL TOOL ASSEMBLY

CROSS-REFERENCE TO RELATED APPLICATION(S)

This application is a continuation of U.S. patent application Ser. No. 17/842,296 filed on Jun. 16, 2022 (published as U.S. Pat. Pub. No. 2022-0313279), which is a continuation application of U.S. patent application Ser. No. 16/266,802 filed on Feb. 4, 2019, now U.S. Pat. No. 11,389,179, which is a divisional application of U.S. patent application Ser. No. 13/469,665 filed May 11, 2012, now U.S. Pat. No. 10,194,922, issued Feb. 5, 2019. The contents of the above referenced applications are incorporated herein by reference in their entirety for all purposes.

FIELD

Various embodiments relate to rotary oscillating bone, cartilage, and disk removal tool assemblies.

BACKGROUND INFORMATION

The prior art has provided rotary bone, cartilage, and disk removal tool assemblies. A problem with rotary bone, cartilage, and disk removal tool assemblies is caused by an encounter with fibrous material, which may wrap about a rotary cutting tool and cause unwanted damage. The prior art has also provided rotary oscillating bone, cartilage, and disk removal tool assemblies.

SUMMARY

According to at least one embodiment, a bone, cartilage, and disk removal tool assembly is provided with a housing. A motor is mounted in the housing. A spindle is mounted for rotation to the housing. A rack-and-pinion mechanism is operably driven by the motor and connected to the spindle to oscillate the spindle for providing a rotary oscillating cutting operation.

According to at least another embodiment, a bone, cartilage, and disk removal tool assembly is provided with a housing. A motor is mounted in the housing. A plurality of cams is supported in the housing and driven for rotation by the motor. A plurality of followers is mounted for rotation to the housing, in engagement with the plurality of cams so that one rotation of the plurality of cams oscillates the plurality of followers more than once while preventing over-rotation of the plurality of followers. A spindle is mounted for rotation to the housing in engagement with the plurality of followers for providing a rotary oscillating cutting operation.

According to at least another embodiment, a bone, cartilage, and disk removal tool assembly is provided with a housing. A motor is mounted in the housing. A spindle is mounted for rotation to the housing. A mechanism is operably driven by the motor and connected to the spindle to oscillate the spindle for providing a rotary oscillating cutting operation. A peak angular acceleration of the spindle is less than nine million radians per second squared.

Other objectives and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

BRIEF DESCRIPTION OF THE FIGURES

FIG. 24 is a chart of values for the transmissions of FIGS. 3 and 14 at various speeds.

DETAILED DESCRIPTION

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

Figure 1:
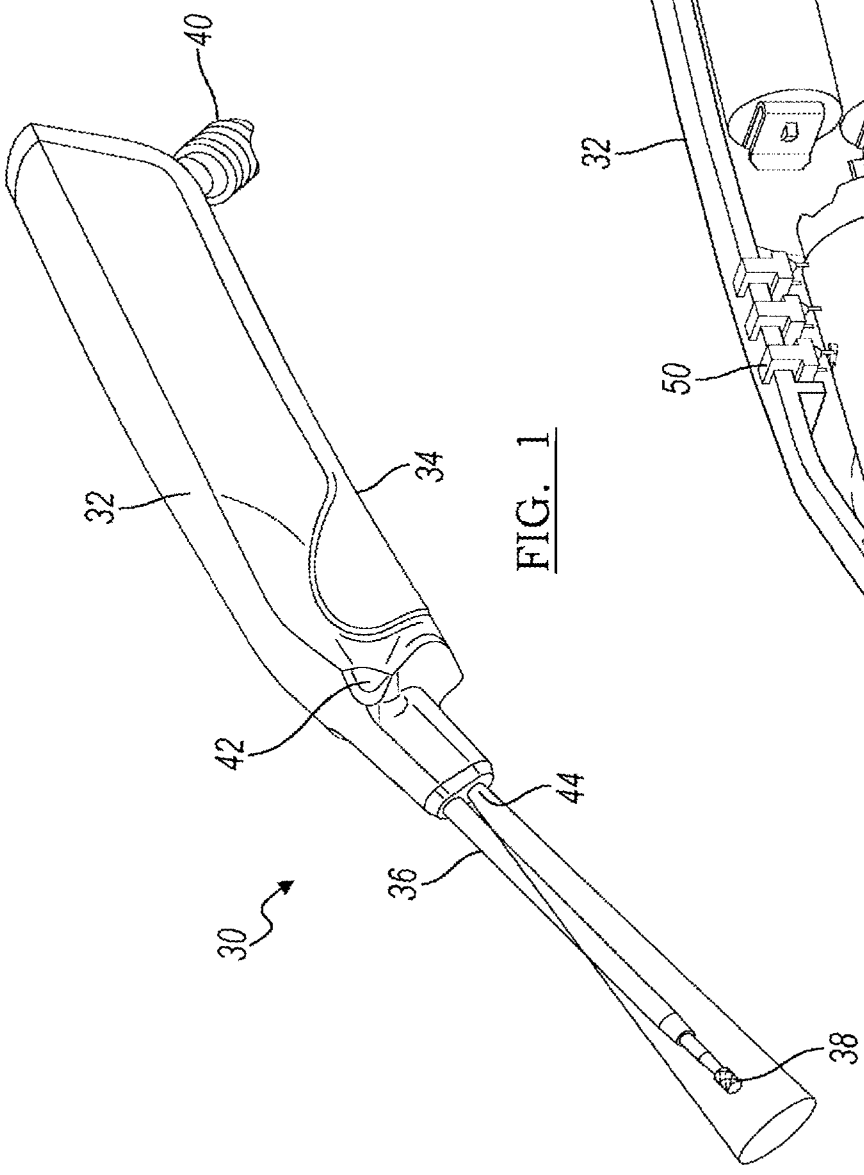
FIG. 1 is a perspective view of a rotary oscillating bone, cartilage, and disk removal tool assembly according to an embodiment.

With reference now to FIG. 1, a rotary oscillating bone, cartilage, and disk removal tool assembly is illustrated according to an embodiment, and referenced generally by numeral 30. The bone, cartilage, and disk removal tool assembly 30 is a handheld tool assembly with a housing 32 providing a handle 34 for manual gripping for bone, cartilage, and disk removal via a cutting operation. Alternatively, the housing may have a narrowed front portion for a smaller pencil-like "precision grip", while the heavier remaining portion is sized to balance on a webspace of the user's hand for allowing better control with less fatigue.

The tool assembly 30 can be used in surgical operations, such as spinal surgery, wherein bone, cartilage, disk, and other non-fibrous body material may be removed, such as from the spine. The tool assembly 30 has an output spindle 36 which is driven to rotate in both directions, or rotary oscillate about its axis. The spindle 36 supports a cutting tool 38, which is driven by the spindle 36 to rotate partially in both directions with a limited range of rotation. Such oscillatory cutting is effective for bone, cartilage, and disk removal by a shearing operation, while effective in minimizing damage to any fibrous material. If the cutting tool 38 inadvertently contacts fibrous material, such as a nerve, during the cutting operation, the fibrous material is likely to be oscillated due to the flexibility of the fibrous material with minimal shearing, thereby minimizing damage to the fibrous material. Such rotary oscillating operations are common in cast removal tools.

The tool assembly 30 may receive power from an external supply, such as a direct current power supply cord 40. A power switch 42 may be provided on the housing for controlling the operation of the tool assembly 30. A light source 44 may also be provided on the housing for illuminating a work piece. The light source 44 may be a light emitting diode (LED).

Figure 2:
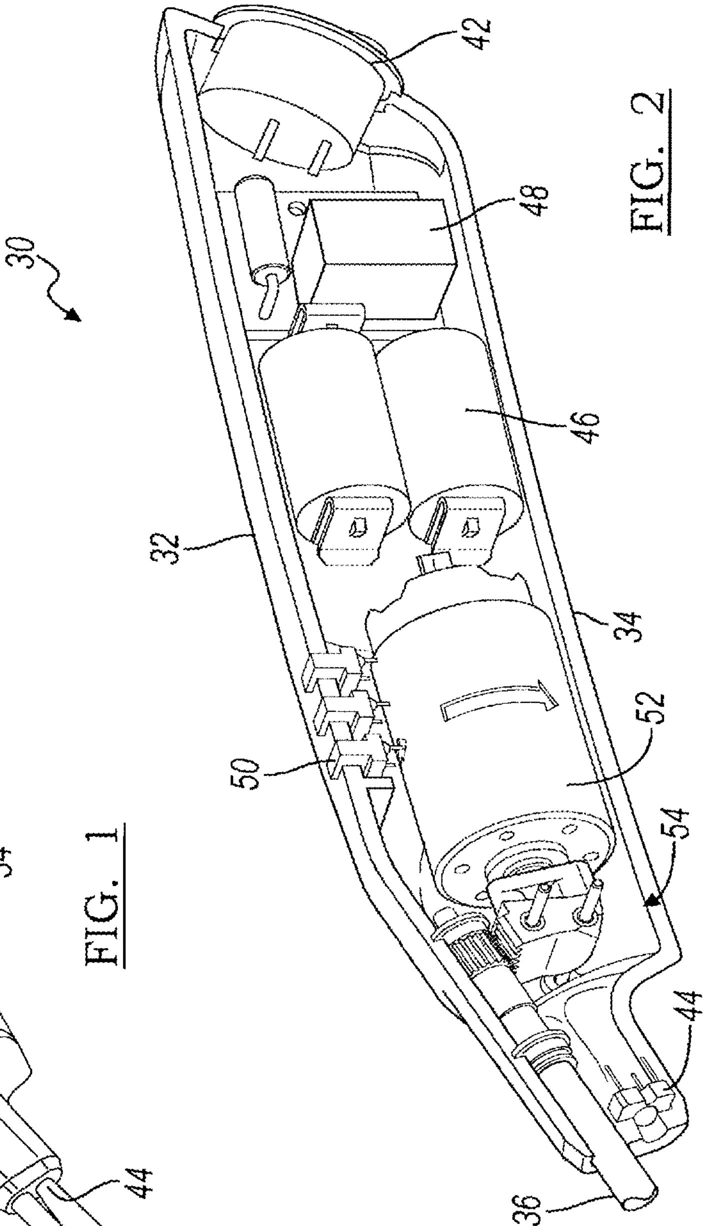
FIG. 2 is a fragmentary perspective view of the tool assembly of FIG. 1.

FIG. 2 illustrates some internal components of the tool assembly 30. A power source may be provided by a battery supply 46 oriented in the housing 32. The battery supply 46 may be charged or recharged by the power cord 40. Electronics 48 are provided in the housing 32 for controlling the operations of the tool assembly 30. The power switch 42 may alternatively be located at a distal end of the housing. A plurality of indicator lamps 50 may be provided on the housing 32 and illuminated by LEDs for indicating operational characteristics of the tool assembly 30, such as a state of charge of the battery supply 46.

A motor 52 is mounted in the housing 32 for providing a rotary input. The motor 52 is powered by the battery supply 46 when controlled by the electronics 48. The motor 52 drives a transmission 54 for converting continuous rotary motion from the motor 52 to rotary oscillation to the spindle 36. The spindle 36 is journalled in the housing 32 and driven by the transmission 54. The spindle 36 may be angled relative to the housing 32, as depicted, for ergonomics. Cooling fins, or a cooling fan, may be attached to or near the motor 52 for cooling the motor 52 and/or the tool assembly 30.

Referring now to FIGS. 2-9, the motor 52 drives an eccentric drive 56. The eccentric drive 56 includes a roller 58 supported to rotate upon the drive 56, which is offset from an axis 60 of the motor 52. Thus, rotation of the eccentric drive 56 causes the roller 58 to revolve about the axis 60. The eccentric drive 56 also includes a counter-balance 62 offset from the axis 60 opposed from the roller 58 to counter-balance the transmission 54 and to minimize unwanted vibrations. The counter-balance 62 can be formed integrally with the eccentric drive 56 according to at least one embodiment. The counter-balance 62 may include an additional weight according to another embodiment. Alternatively, the roller 58 may be a pin.

A guide 64 is supported in the housing 32 generally perpendicular to the motor axis 60. The guide 64 can be provided by a pair of pins 66. A shuttle 68 is provided on the guide 64 for reciprocating translation upon the guide 64. The shuttle 68 includes a channel 70 that is generally perpendicular to the guide 64. The channel 70 receives the roller 58 of the eccentric drive 56. The channel 70 cooperates as a follower for permitting the roller 58 to translate along a length of the channel 70 while driving the shuttle 68 along the guide 64. The guide 64 may utilize bearings and/or rollers to reduce friction.

The eccentric drive 56 and shuttle 58 cooperate as a Scotch-yoke mechanism for converting continuous rotary motion to linear reciprocating motion. The range of motion is illustrated in FIGS. 4-9. At FIG. 4, the roller 58 is at bottom-dead-center, thereby maximizing translation of the shuttle 68. From FIGS. 5 to 6, the roller 58 approaches an extent of the translation, whereby the shuttle 68 decelerates. From FIGS. 6 to 7, the shuttle 68 reverses direction and accelerates. At FIG. 8, the roller 58 approaches top-dead-center at a maximum velocity of the shuttle 68. From FIG. 8 to FIG. 9, the shuttle 68 decelerates until it reaches an opposite range of translation, whereby the shuttle 68 reverses directions and continues to the position of FIG. 4. Although the Scotch-yoke mechanism is illustrated, any mechanism for converting rotary motion to reciprocation can be employed, such as a crank-and-slider mechanism, or the like.

Referring again to FIGS. 2-9, a gear rack 72 is formed upon the shuttle 68. The gear rack 72 is formed generally parallel to the spindle 36. A pinion gear or burr gear 74 is mounted to the spindle 36 in engagement with the gear rack 72, thereby providing a rack-and-pinion mechanism for converting the reciprocating translation of the shuttle 68 to rotary oscillation of the spindle 36. A pair of bearing assemblies 76 may also be provided in the housing for providing bearing support to the spindle 36. The transmission 54 may include any additional gear sets, as is known in the art, to vary speed or torque. According to one embodiment, a spur gear may be added to a motor output shaft to multiply speed of the roller 58.

Figure 10:
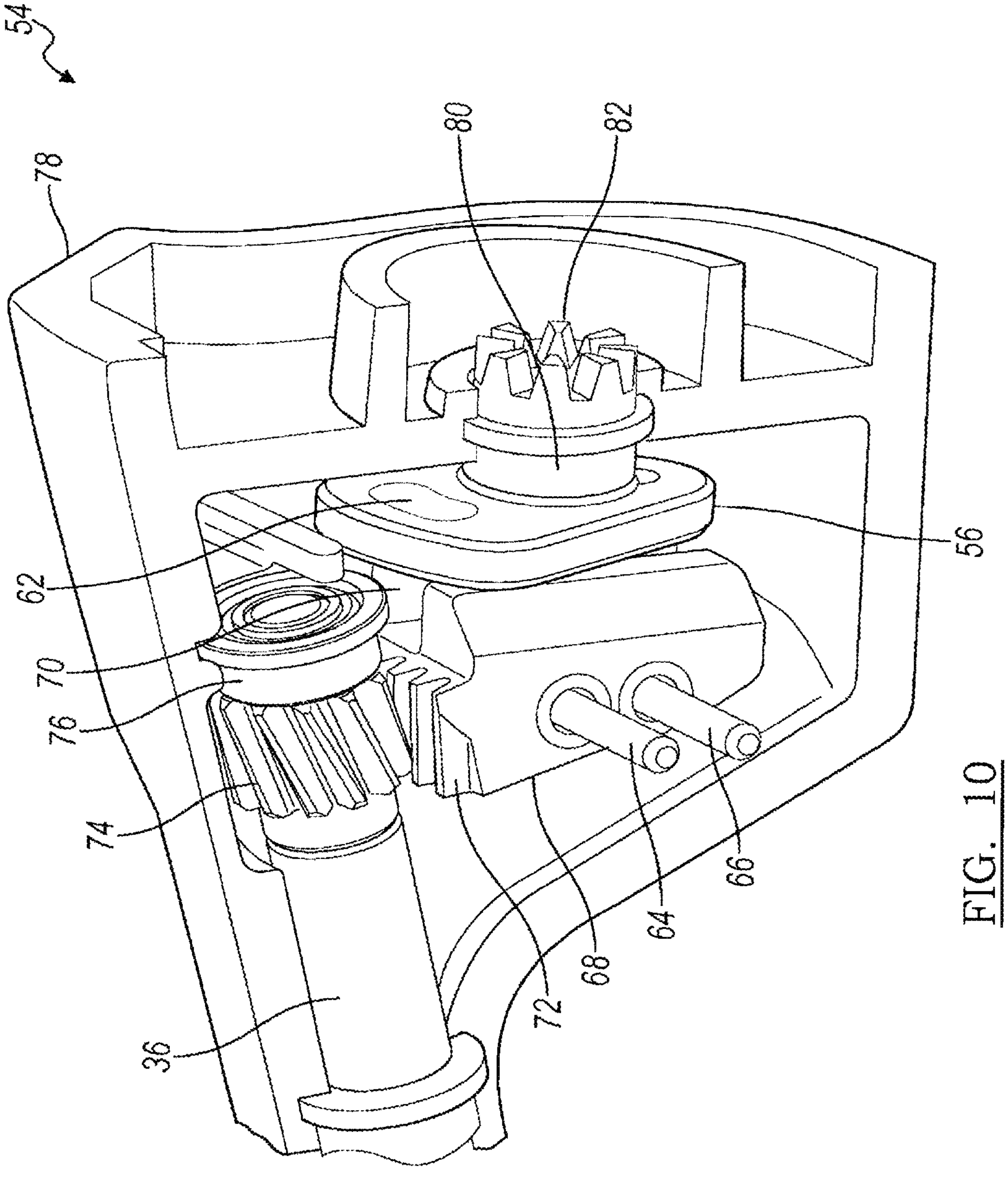
FIG. 10 is an enlarged fragmentary perspective view of a transmission of the tool assembly of FIG. 1, according to another embodiment.

FIG. 10 illustrates the transmission 54 according to another embodiment. A front housing portion 78 may be detachable from the remainder of the housing 32 for interchanging functionalities of the tool assembly 30. A bearing assembly 80 is provided in the front housing portion 78 for providing bearing support of the eccentric drive 56. A first coupling configuration 82 is exposed from the front housing portion 78 to engage a corresponding second coupling configuration on the housing 32. Thus, the transmission 54 and output spindle 36 can be detached and reattached to the housing 32.

Figure 11:
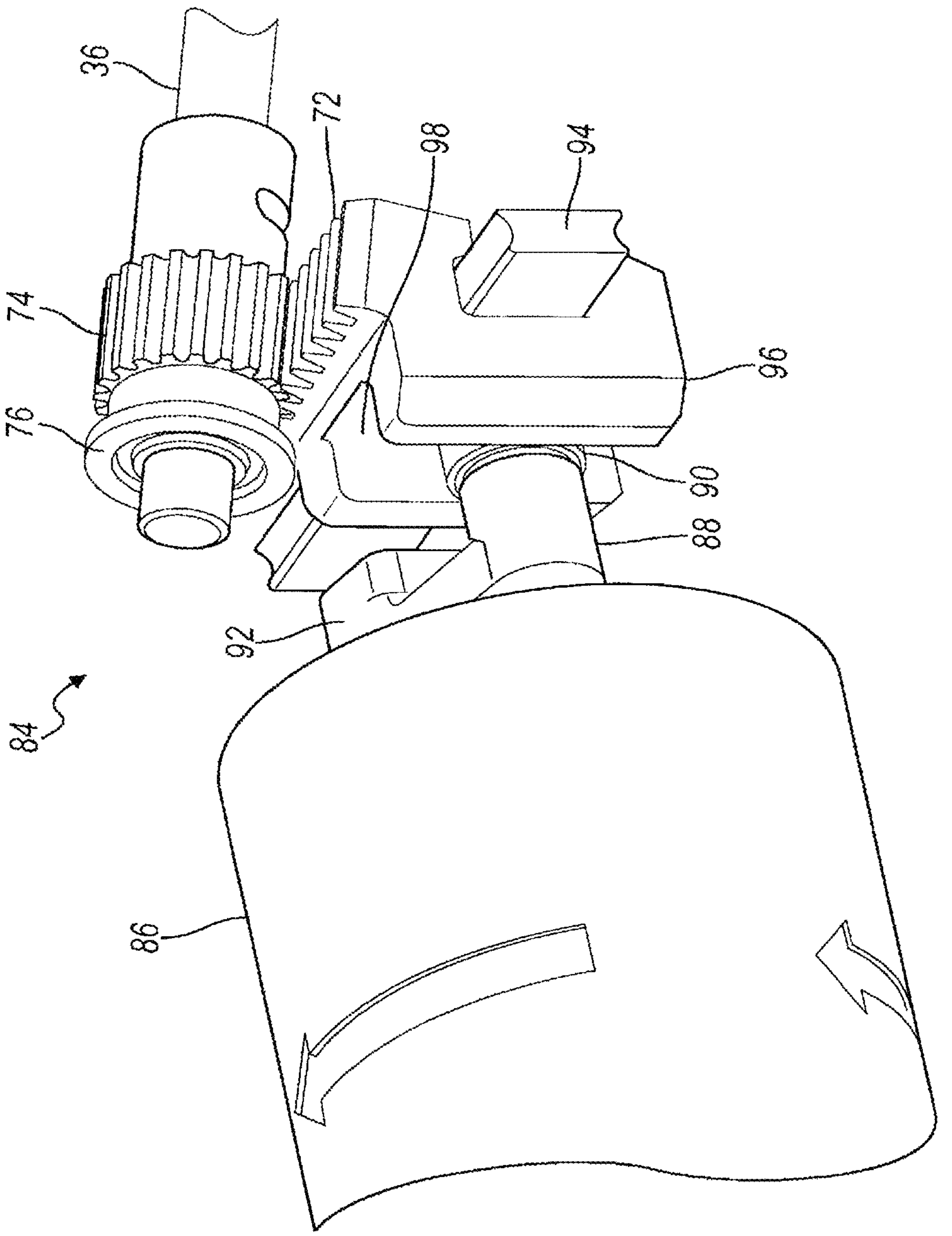
FIG. 11 is an enlarged partial perspective view of a transmission of the tool assembly of FIG. 1, according to yet another embodiment.

FIG. 11 illustrates a transmission 84 according to another embodiment. A motor 86 drives an eccentric drive 88 with an offset roller 90 and a counter-balance 92. A guide is provided by a rail 94 in the housing 32. A shuttle 96 is provided on the rail 94, and includes a channel 98 for receiving the roller 90. Ball bearings can be provided between the shuttle 96 and the rail 94.

Unlike prior art rotary oscillating bone, cartilage, and disk removal tool assemblies, the tool assembly 30 reduces vibrations to the user, and the tool assembly 30 is easier to grip during cutting operations. In order to obtain these product performance objectives, the motion of the cutting tool 38 avoids sudden or abrupt changes in direction or velocity. Instead, as the cutting tool 38 oscillates back and forth, its velocity smoothly transitions from zero to its peak value, then back to zero and repeats. The motion of the cutting tool 38 is controlled so that angular displacement, velocity and acceleration all follow harmonic signatures. That is to say, when plotted on a graph, these characteristics follow a sinusoidal-like curve. Of course, non-harmonic signatures may be employed.

The lateral displacement, velocity and acceleration of the shuttle 96 can be found at any point in time by the following equations.

Motor velocity: $\omega=2\pi(15000\ \text{rpm}/60)=1570.8$ radians/second); wherein rpm is rotations per minute.

$$\text{Motor Angle: } \theta = \omega t; \text{ wherein } t \text{ is time.}$$

Displacement: $x_{shuttle}=R\sin(\omega t)$; wherein R is an offset of the roller 90 from the motor axis 60. For the depicted embodiment, R equals 3.75 millimeters (mm).

$$\text{Shuttle Velocity: } v_{shuttle} = \omega R\cos(\omega t).$$

$$\text{Shuttle Acceleration: } a_{shuttle} = -\omega^2 R\sin(\omega t).$$

The burr gear 74 is driven by the shuttle 68 via the gear rack 72. The burr gear 74 demonstrates similar motion, but instead of lateral displacement, it experiences angular displacement. The rotational motion of the burr gear 74 can be described by the following equations:

Angular Displacement: $x_{burr}=(R/R_{burr})\sin(\int t)$; wherein $R_{burr}$ is pitch radius of burr gear, which for the depicted embodiment is three millimeters.

$$\text{Angular Velocity: } v_{burr} = \omega\left({}^{R}/R_{burr}\right)\cos(\omega t).$$

Peak Angular Velocity: $v_{burr}(\text{peak})=n\omega\sigma$, wherein $\sigma$ is the oscillation amplitude, which is ½ of the total angular range (expressed in radians), and which for the depicted embodiment is also equal to $R_{burr}$; and n is the number of oscillations per motor revolution, which for the depicted embodiment is one.

$$\text{Angular Acceleration: } a_{burr} = -\omega^2\left({}^{R}/R_{burr}\right)\sin(\omega t).$$

$$\text{Peak Angular Acceleration: } a_{burr}(\text{peak}) = (n\omega)^2\sigma.$$

$$\text{Peak Angular Jerk: } j_{burr}(\text{peak}) = (n\omega)^3\sigma.$$

Figure 12:
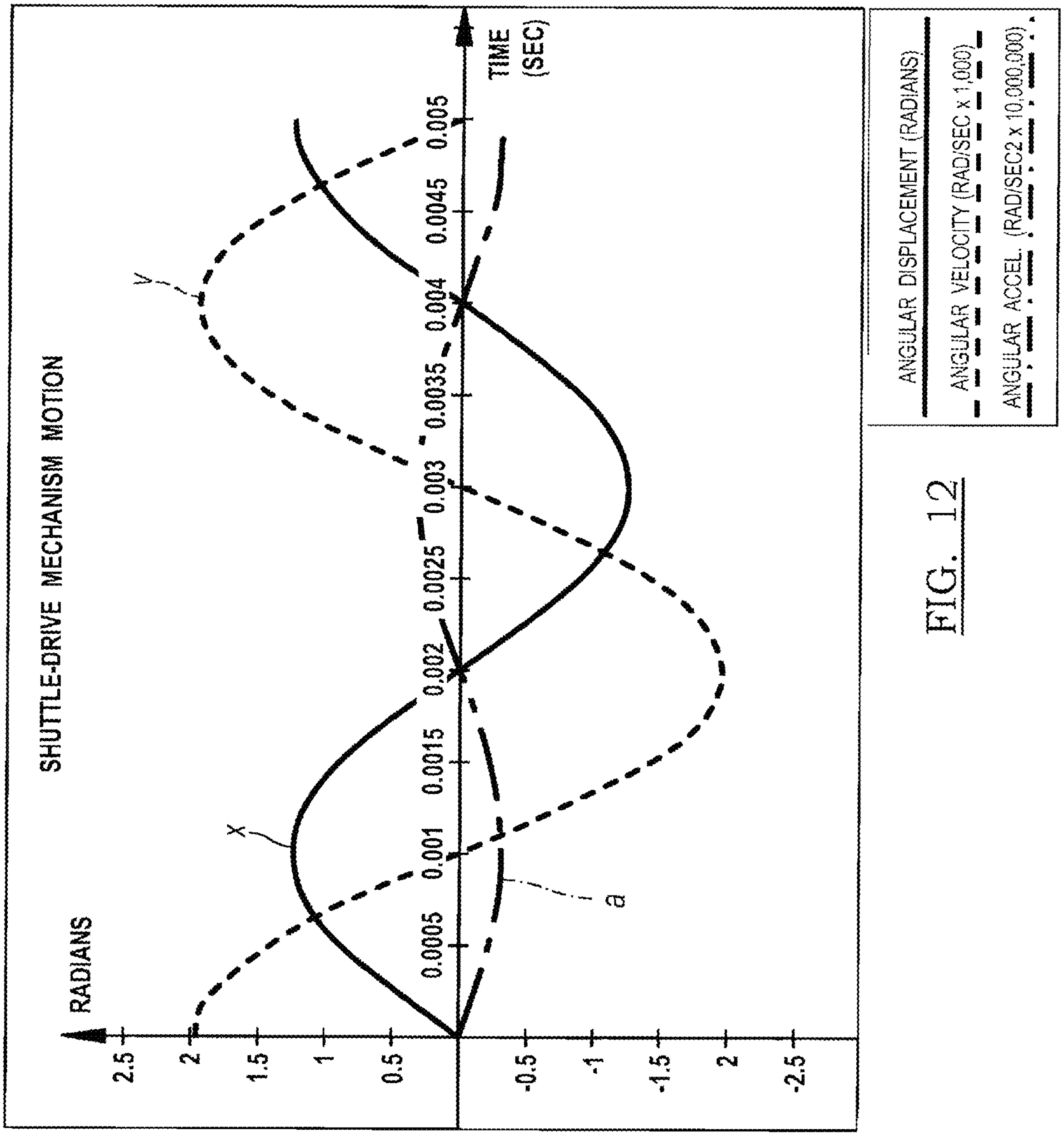
FIG. 12 is a graph of displacement, velocity and acceleration of the tool assembly of FIG. 11.

FIG. 12 illustrates a graph of angular displacement x, angular velocity v, and angular acceleration α. At 15,000 rpm, the motor 86 completes one revolution every 0.004 seconds. As the curve x illustrates, the burr gear 74 completes one full oscillation during one motor revolution. Oscillation is rotation from center, away from center to one angular side, rotation past center to another angular side, and back to center. The burr gear 74 also travels±1.25 radian (±71.6°) per oscillation (143.2° total travel).

Curve v shows that the peak angular velocity (VP=1,963 rad/sec=18,750 rpm) occurs at top dead and bottom dead center, exactly in the middle of the burr gear 74 swing. This is when the maximum amount of material is being removed from the material being cut. The shuttle 96 then allows the burr gear 74 to decelerate to a velocity of zero as it approaches maximum excursion, only to accelerate back through to maximum velocity on the return swing.

The motion of the burr gear 74 is smooth, with no sudden or abrupt changes in direction, velocity or acceleration. Although the motion of the depicted embodiment can be described with formulas in terms of sine and cosine, the design could be embodied in such a way that the motion of the burr gear 74 follows similarly looking harmonic curves that cannot be conveniently described with formulas in terms of sine and cosine.

Curve a illustrates that a peak angular acceleration of the spindle is less than five million radians per second squared at fifteen-thousand oscillations per minute. By analyzing the rate of change of acceleration, jerk can be determined as less than five billion radians per second cubed at fifteen-thousand oscillations per minute.

Although the motor speed is described as 15,000 rpm, the motor speed may be within a range of 5,000 rpm to 40,000 rpm according to one embodiment. The motor speed may be within a range of 15,000 rpm to 20,000 rpm according to another embodiment.

The transmission 84 in the tool assembly 30 causes the output torque at the burr gear 74 to vary from the input torque of the motor 86. This variance can be expressed as a Torque Ratio:

$$X_T = \frac{T_{burr}}{T_m};$$

wherein $T_{burr}$ is output torque applied to burr gear 74; and $T_m$ is input torque supplied by the motor 86.

In other words, the transmission 84 causes the output torque to the burr gear 74 to be "$X_T$ times" the input torque from the motor 86 at any specified point in the displacement of the burr gear 74. This factor is a mechanical advantage of the transmission 84. The following analysis does not take into account inefficiencies (such as friction, air resistance and other losses) that will impede the transmission of torque from the motor 86 to the burr gear 74. However, steps have been taken to reduce such losses wherever possible, such as the use of bearings to reduce friction.

In general, Torque equals Force times Distance. The torque of the motor 86 acts on the eccentric drive 88, which then exerts a force on the shuttle 96 via the roller 90. The forces between the shuttle 96 and the roller 90 are equal and opposing, and in a direction perpendicular to the shuttle channel 98. The motor torque can therefore be expressed as this force multiplied by its perpendicular distance from the eccentric drive 88:

$T_m=F_pR\cos(\theta)$; wherein $F_p$ equals $F_s$, which are forces acting between the roller 90 and the shuttle 96.

Figure 6:
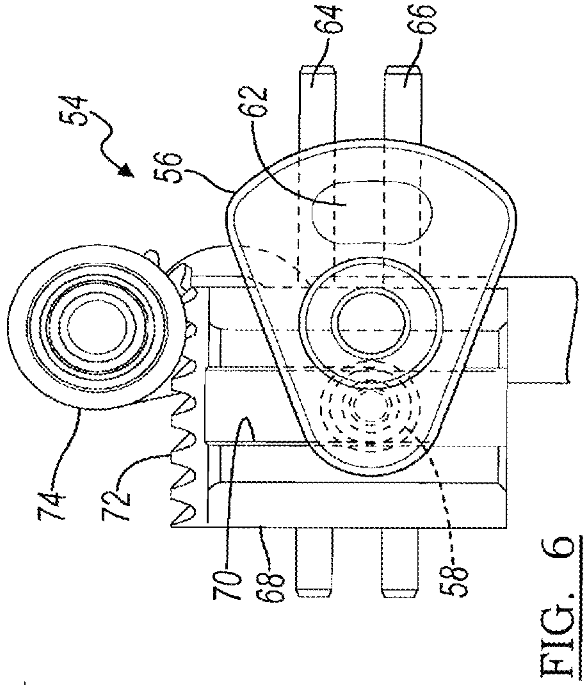
FIG. 6 is another axial schematic view of the transmission of FIG. 3, illustrating a third position.
Figure 4:
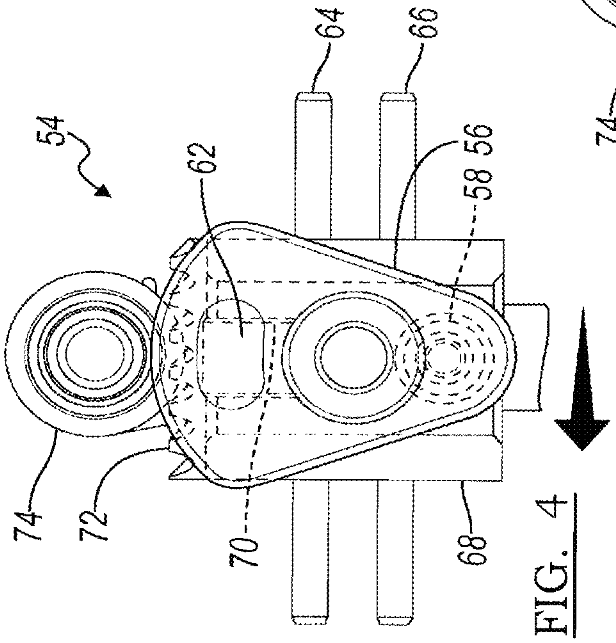
FIG. 4 is an axial schematic view of the transmission of FIG. 3, illustrating a first position.
Figure 8:
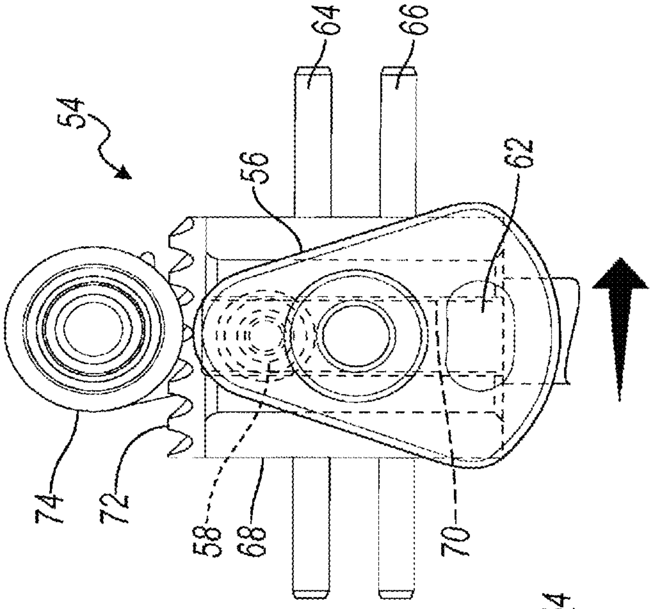
FIG. 8 is another axial schematic view of the transmission of FIG. 3, illustrating a fifth position.
Figure 9:
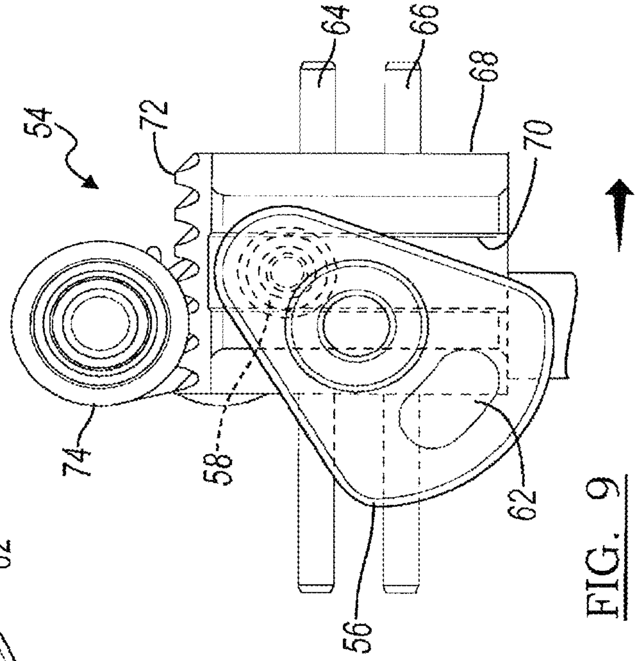
FIG. 9 is another axial schematic view of the transmission of FIG. 3, illustrating a sixth position.
Figure 7:
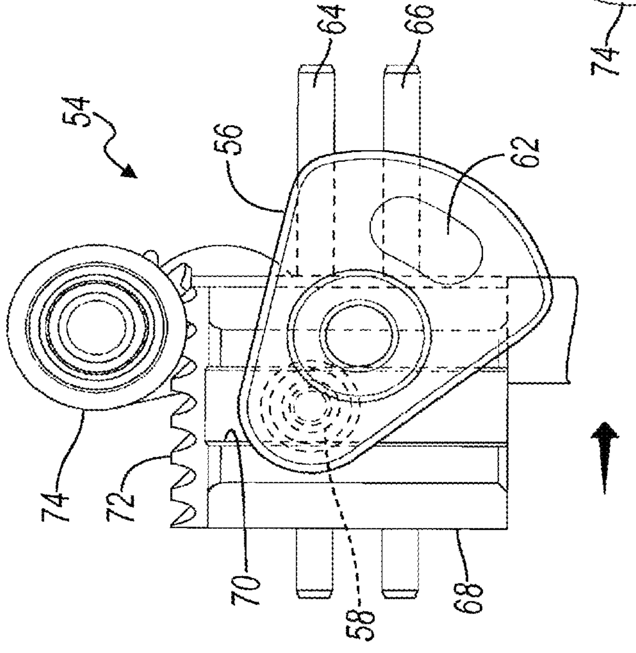
FIG. 7 is another axial schematic view of the transmission of FIG. 3, illustrating a fourth position.

When the shuttle 96 and the burr gear 74 approach a travel limit (as depicted in FIG. 6 for shuttle 68), the velocity of the shuttle 96 and the burr gear 74 is low compared to the velocity of the eccentric drive 88. Since the eccentric drive

88 has to move a relatively large angle in order to move the shuttle 96 and the burr gear 74 a relatively small amount, it has a "mechanical advantage" with respect to torque. In other words, the eccentric drive 88 is able to transfer much more torque to the burr gear 74 just when it is needed most-when the burr gear 74 is moving its slowest and is the most likely to get stuck. The length of "R cos (0)" decreases as the shuttle 96 nears its end of travel, and as its formula suggests, the Torque Ratio increases.

As the roller 90 pushes on the shuttle 96, the shuttle 96 pushes on the burr gear 74 with the same amount of force. This force creates a torque on the burr gear 74 which can be expressed as:

$T_{burr}=F_{burr}R_{burr}$; wherein $F_{burr}$ equals $F_s$, which equals forces acting between the burr gear 74 and the shuttle 96. $R_{burr}$ equals a pitch radius of the burr gear 74, which is three millimeters for the depicted embodiments. Combining the above equations, the torque on the burr gear 74 can be expressed as:

$$T_{burr} = T_m \frac{R_{burr}}{R\cos(\theta)}.$$

Therefore, the Torque Ratio can be expressed as:

$$X_T = \frac{R_{burr}}{R\cos(\theta)}.$$

Figure 13:
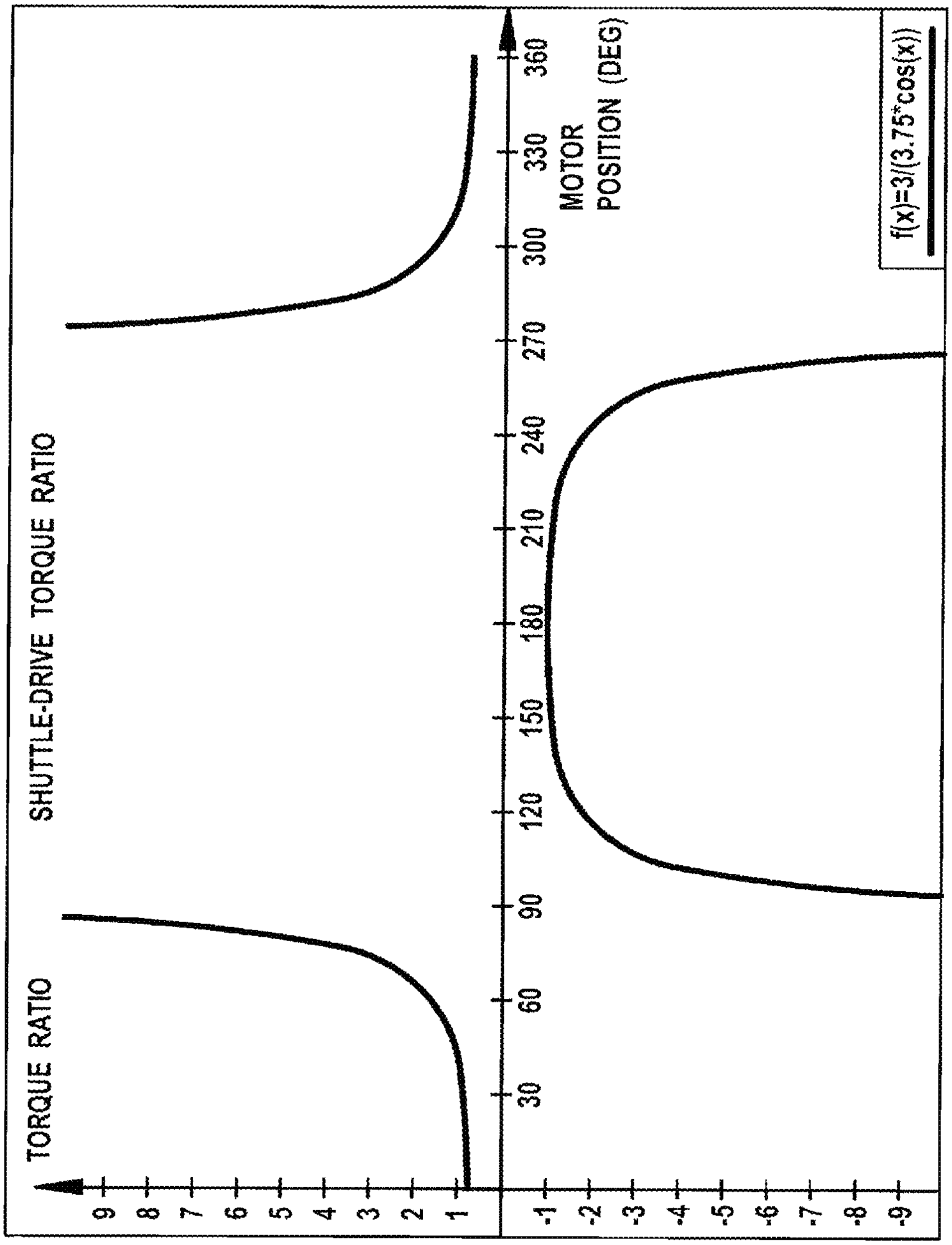
FIG. 13 is a graph of torque of the tool assembly of FIG. 11.

FIG. 13 illustrates a torque ratio of the burr gear 74. The minimum torque applied to the burr gear 74 equals 0.80 times (or eighty percent of) the motor torque. This minimum torque occurs at the midpoint of the travel of the burr gear 74, when its velocity is greatest. As the burr gear angular velocity decreases toward zero, the transmitted torque increases exponentially toward infinity (theoretically, it would never actually obtain infinity due to the inefficiencies that have been ignored).

This relationship between torque and velocity is well known. In general, the Torque Ratio is inversely proportional to the Velocity Ratio. For the embodiment of FIG. 11, the angular velocity of the burr gear 74 can be rewritten in terms of θ (knowing that θ=ωt):

$$v_{burr} = \omega\left({}^{R}/R_{burr}\right)\cos(\omega t) \text{ becomes } v_{burr} = \omega\left({}^{R}/R_{burr}\right)\cos(\theta).$$

Then the Velocity Ration is:

$$X_v = \frac{v_{burr}}{\omega} = \frac{R\cos(\theta)}{R_{burr}};$$

which is the inverse of the Torque Ratio:

$$X_T = \frac{R_{burr}}{R\cos(\theta)} = \frac{1}{X_v}$$

A dampening system may be provided in the tool assembly 30 to control vibration. The dampening system may include a dampening material or system between the motor 52 or transmission 54 and the housing 32 to minimize vibrations to the user. The dampening system or material can be provided externally or internally on the housing 32.

Figure 14:
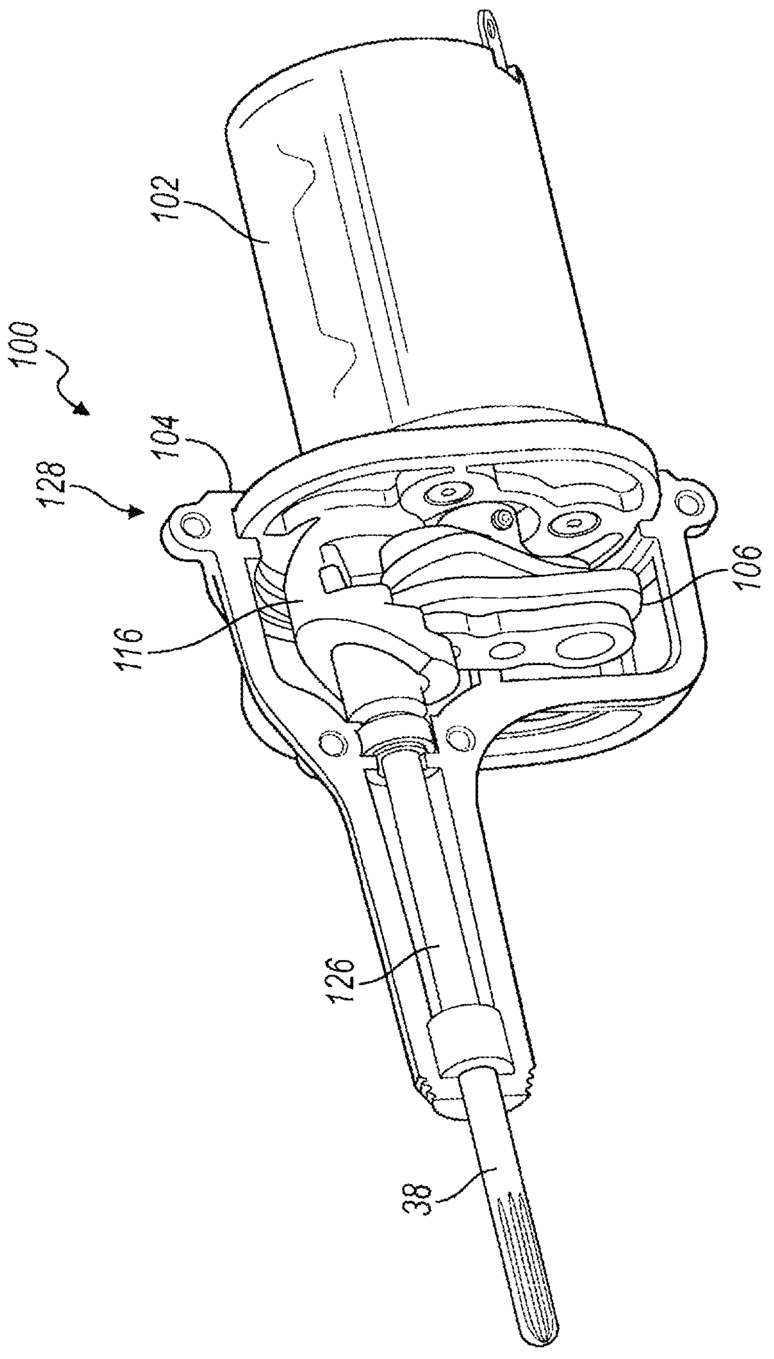
FIG. 14 is a fragmentary perspective view of a transmission of the tool assembly of FIG. 1 according to another embodiment.

FIG. 14 illustrates a bone, cartilage, and disk removal tool assembly 100 according to another embodiment. The tool assembly 100 includes a motor 102 mounted in a housing 104. The motor 102 drives a cam mechanism 106 for continuous rotation. The cam mechanism 106 has four distinct cam profiles 108, 110, 112, 114 stacked axially from the motor 102. Each of the cam profiles 108, 110, 112, 114 is illustrated schematically in FIGS. 15-18. A follower mechanism 116 is mounted for rotation in the housing 104. The follower mechanism 116 has four follower profiles 118, 120, 122, 124, each for cooperating with one of the cam profiles 108, 110, 112, 114, as also illustrated in FIGS. 15 to 18. A spindle 126 is provided in the housing 104 with bearing support. The cam mechanism 106 and the follower mechanism 116 cooperate as a transmission 128 for converting one rotation of the cam mechanism into two rotary oscillations of the follower mechanism 116.

The electric motor 102 spins the cam mechanism 106 continually in one direction, which is clockwise in FIGS. 15-18. The cam profiles 108, 110, 112, 114 engage the follower profiles 118, 120, 122, 124 at two contact points at all times. At one contact point, the cam mechanism 106 pushes the follower mechanism 116 to rotate. At the other contact point, the cam mechanism 106 prevents the follower mechanism 116 from over-rotating. The profiles 108, 110, 112, 114 on the cam mechanism 106 work together to cause the follower mechanism 116 to rotationally oscillate in two directions. For the depicted embodiment, each of the four cam profiles 108, 110, 112, 114 consists of two symmetrical lobes, which causes the follower mechanism 116 to make two complete oscillations (back and forth twice) for every complete revolution of the motor 102. The cam mechanism 106 could also be designed asymmetrical, and/or so that it causes the follower mechanism 116 to make any number of oscillations, such as one, or more than two, per motor revolution.

Figure 16:
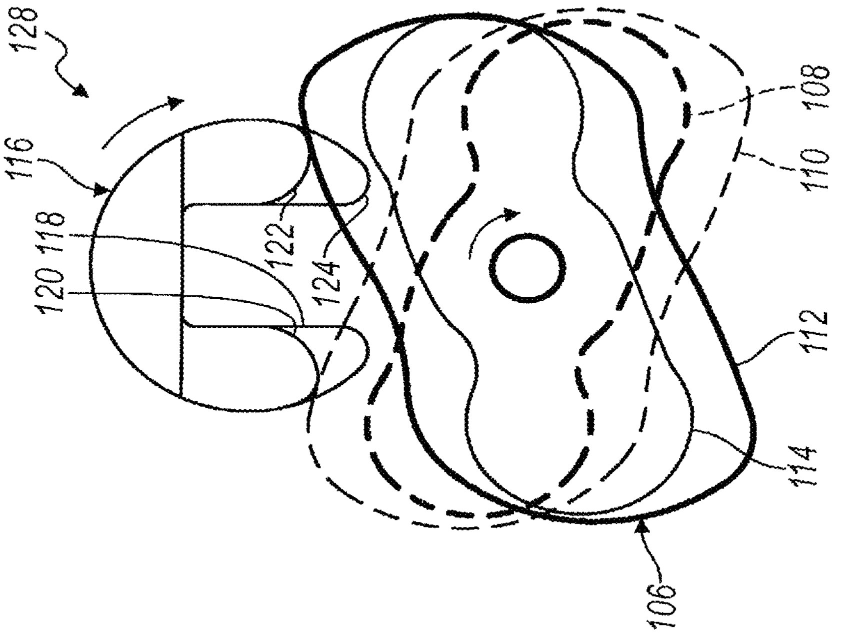
FIG. 16 is another axial schematic of the transmission of FIG. 14 illustrated in a second position.
Figure 15:
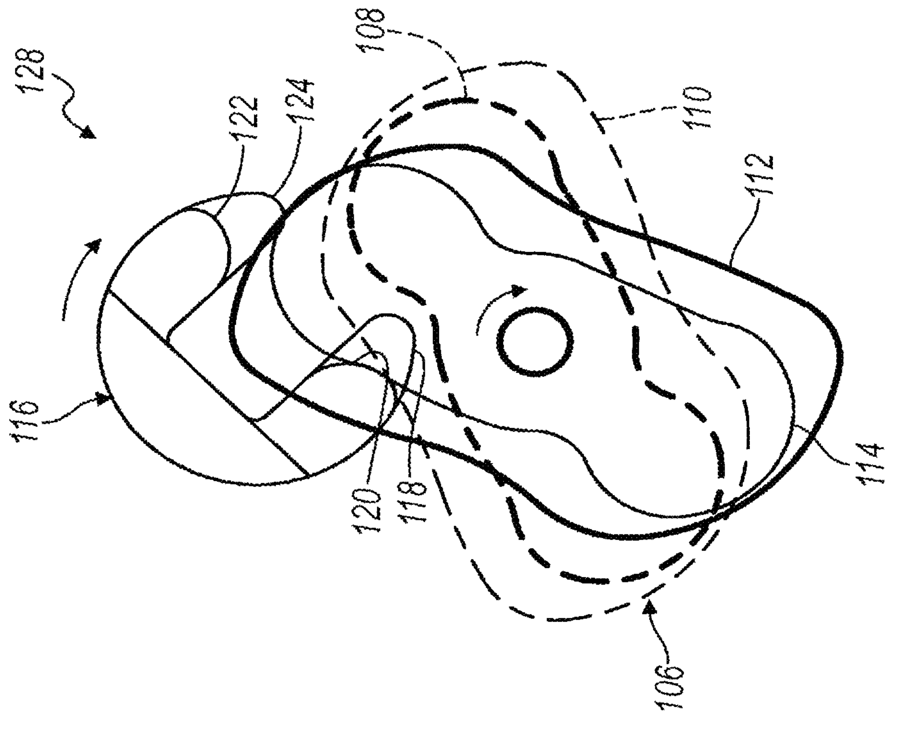
FIG. 15 is an axial schematic of the transmission of FIG. 14 illustrated in a first position.
Figure 18:
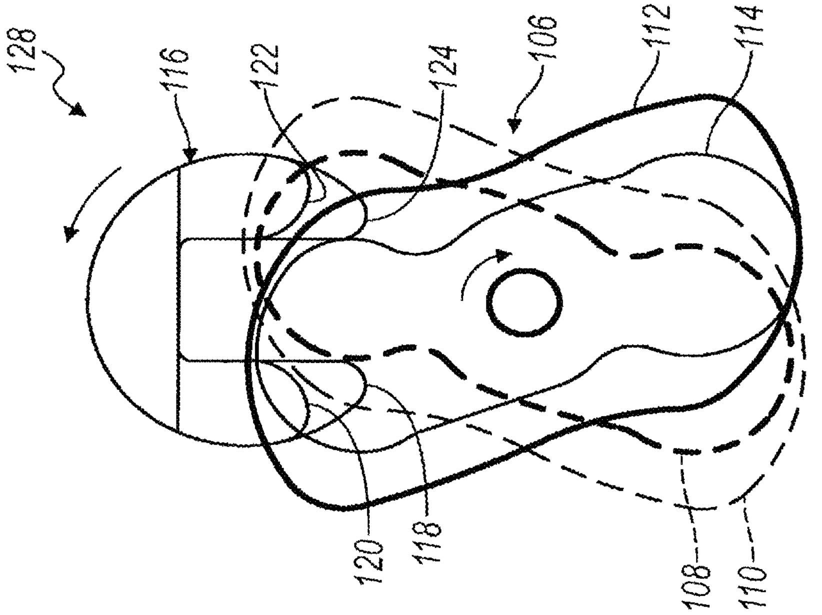
FIG. 18 is another axial schematic of the transmission of FIG. 14 illustrated in a fourth position.
Figure 17:
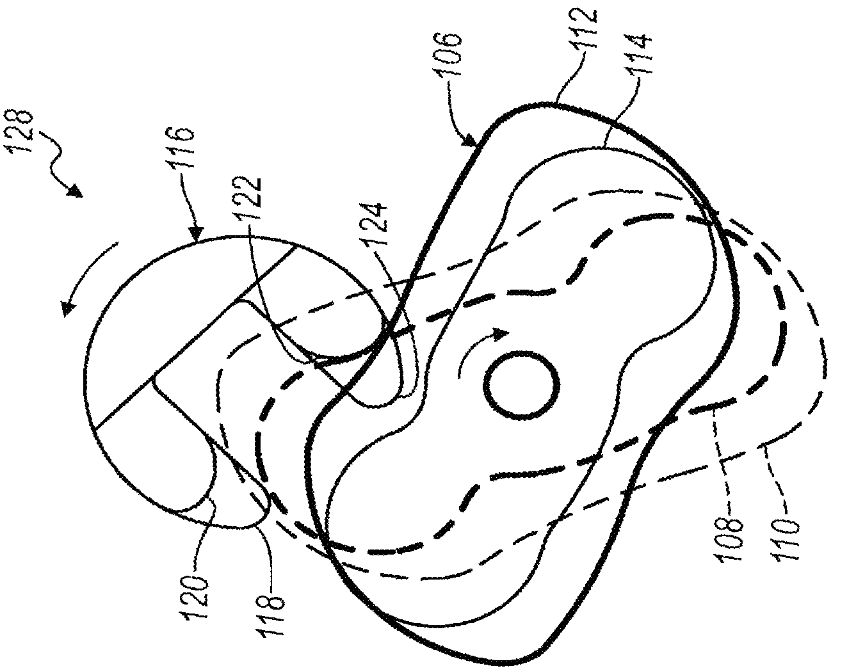
FIG. 17 is another axial schematic of the transmission of FIG. 14 illustrated in a third position.

In FIG. 15, the second cam profile 110 contacts the second follower profile 120 for preventing over-rotation of the follower mechanism 116, while the fourth cam profile 114 drives the fourth follower profile 124. In FIG. 16, the second cam profile 110 contacts the second follower profile 120 for driving the follower mechanism 116, while the third cam profile 112 engages the third follower profile 122 to prevent over-rotation of the follower mechanism. In FIG. 17, the first cam profile 108 contacts the first follower profile 118 for preventing over-rotation of the follower mechanism, while the third cam profile 112 drives the third follower profile 122, thereby reversing directions. In FIG. 18, the first cam profile 108 contacts the first follower profile 118 to prevent over-rotation of the follower mechanism 116, while the fourth cam profile 114 drives the fourth follower profile 124. The process is repeated at FIG. 15.

The cam profiles 108, 110, 112, 114 cause the angular displacement, velocity and acceleration of the follower mechanism 116 to follow sinusoidal wave patterns. The motion can be described:

Angular Displacement: $x_{burr}=\sigma\ \sin(n\omega t)$; wherein n equals the number of full oscillations per motor revolution, which is two for the depicted embodiment. σ equals half of the full oscillation range (forty-five degrees or π/4 radian).

$$\text{Angular Velocity: } V_{burr} = n\omega\sigma\cos(n\omega t).$$

-continued $$\text{Peak Angular Velocity: } v_{burr}(\text{peak}) = n\omega\sigma.$$

$$\text{Angular Acceleration: } a_{burr} = -(n\omega)^2\sigma\sin(n\omega t).$$

$$\text{Peak Angular Acceleration: } a_{burr}(\text{peak}) = (n\omega)^2\sigma.$$

$$\text{Peak Angular Jerk: } j_{burr}(\text{peak}) = (n\omega)^3\sigma.$$

Figure 19:
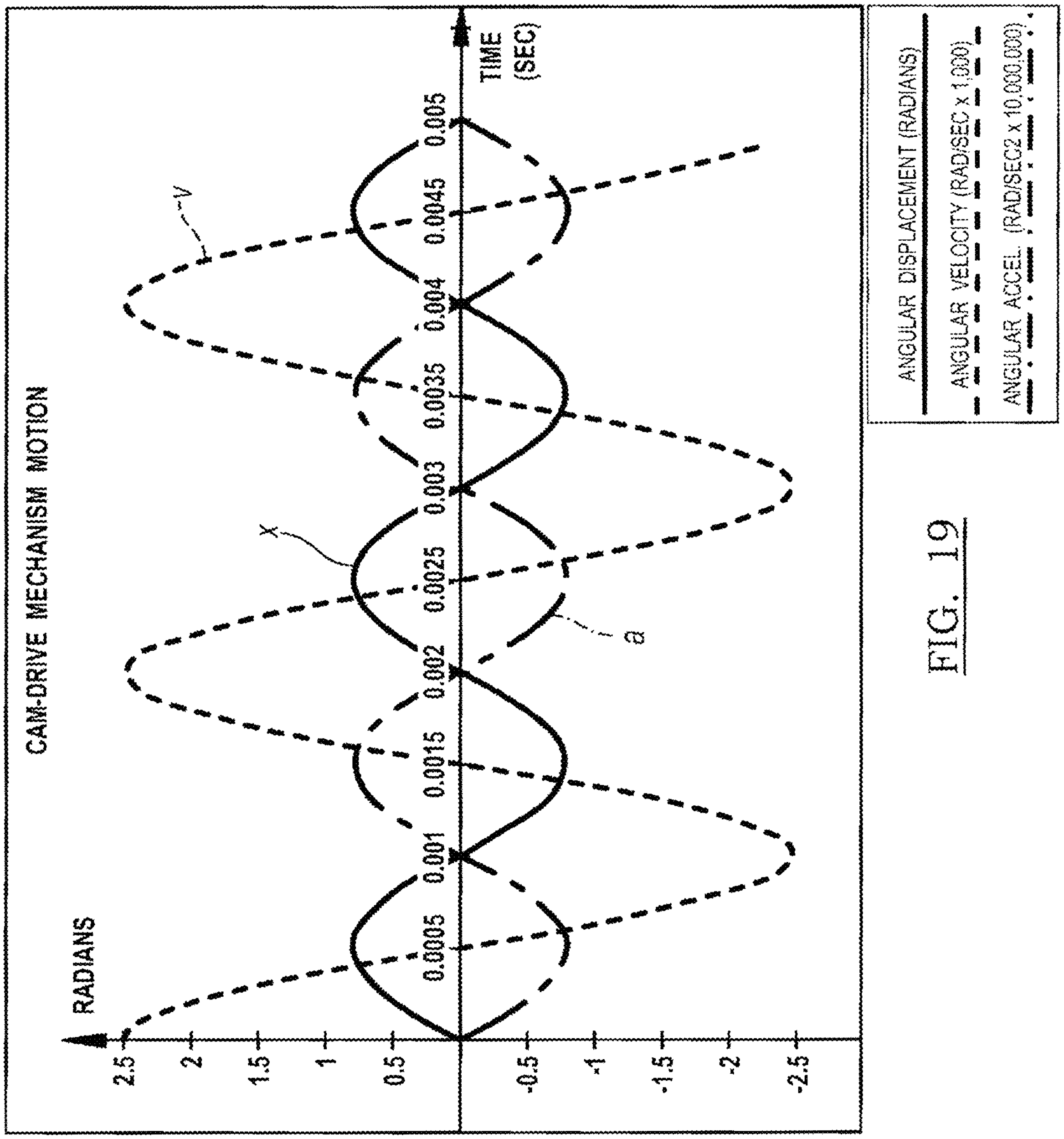
FIG. 19 is a graph of displacement, velocity, and acceleration of the transmission of FIG. 14.

FIG. 19 illustrates these relationships. At 15,000 rpm, the motor 102 completes one revolution every 0.004 seconds. Displacement curve x illustrates that the follower mechanism 116 completes two full oscillations during one motor revolution. The follower mechanism 116 also travels ±0.79 radian (±45 degrees) per oscillation (ninety degrees total travel). Velocity curve v illustrates the peak angular velocity to be ($V_P$=2,467 rad/sec=23,562 rpm), which is higher than the prior embodiment. The peak angular velocity occurs in the middle of the oscillation, when the maximum amount of material is being removed from the material being cut. The motion of the follower mechanism 116 is smooth, with no sudden or abrupt changes in direction, velocity or acceleration. Similarly, although the motion of the current design can be described with formulas in terms of sine and cosine, the design could be changed in such a way that the motion of the follower mechanism 116 follows similarly looking harmonic curves that cannot be conveniently described with formulas in terms of sine and cosine.

Curve a illustrates that a peak angular acceleration of the spindle is less than eight million radians per second squared at thirty-thousand oscillations per minute. By analyzing the rate of change of acceleration, jerk can be determined as less than twenty-five billion radians per second cubed at thirty-thousand oscillations per minute.

Since the cam mechanism 106 is attached directly to the motor 102, the torque on the cam mechanism 106 is equal to the torque of the motor 102. This torque can be expressed as a force acting at a perpendicular distance from the center of the cam mechanism 106. The following analysis does not take into account inefficiencies (such as friction, air resistance and other losses) that will impede the transmission of torque from the motor 102 to the spindle 126. However, steps have been taken to reduce such losses wherever possible, such as the use of bearings to reduce friction.

$T_m=F_cL_c\cos(A_c)$; wherein $F_c$ equals force of cam mechanism 106 acting on a cam follower 108, 110, 112, 114. $L_c$ equals a length of cam contact point from center. $A_c$ equals a push angle of cam profile, which is an angle normal from the contact point to the center.

In the case of the follower mechanism 116, the torque on the follower mechanism 116 is equal to the torque on the burr or cutting tool driven by the spindle 126, and can be expressed as:

$T_{burr}=F_fL_f\cos(A_f)$; wherein $F_f$ equals a force of follower acting on cam; $L_f$ equals a length of follower contact to center; and $A_f$ equals push angle of follower profile, which is an angle normal form the contact point to the center.

The maximum amount of torque that can be transmitted to the spindle 126 occurs during a steady state situation, such as if the spindle 126 becomes stuck. In such a situation, the forces acting between the cam mechanism 106 and the follower mechanism 116 are equal and opposing, and in a line perpendicular to a line that is tangent to the point of contact:

$$F_c = F_f$$

Combining the above equations, the torque on the spindle 126 or cutting tool burr can be expressed as:

$$T_{burr} = T_m\frac{L_f\cos(A_f)}{L_c\cos(A_c)}.$$

Therefore, for this embodiment, the Torque Ratio can be expressed as:

$$X_T = \frac{L_f\cos(A_f)}{L_c\cos(A_c)}.$$

When the follower mechanism 116 nears its end of travel, the velocity of the follower mechanism 116 is low compared to the velocity of the cam mechanism. Since the cam mechanism 106 has to move a relatively large angle in order to move the follower mechanism 116 a relatively small angle, it has a "mechanical advantage" with respect to torque. In other words, the cam mechanism 106 is able to transfer much more torque to the follower mechanism 116 just when it is needed most-when the follower mechanism 116 is moving its slowest and is the most likely to get stuck. As the formula suggests, the Torque Ratio increases as the length of "$L_f\cos(A_f)$," increases, and the length of "$L_c\cos(A_c)$" decreases.

The Torque Ratio can also be computed by taking the inverse of the Velocity Ratio. The angular velocity of the spindle 126 or output burr can be rewritten in terms of θ (knowing that θ=ωt):

$$V_{burr} = n\omega\sigma\cos(n\omega t) \text{ becomes } V_{burr} = n\omega\sigma\cos(n\theta).$$

Then the Velocity Ratio is:

$$X_v = \frac{v_{burr}}{\omega} = n\sigma\cos(n\theta).$$

The Torque Ratio, being the inverse of the Velocity Ratio, becomes:

$$X_T = \frac{1}{X_v} = \frac{1}{n\sigma\cos(n\theta)}.$$

Figure 20:
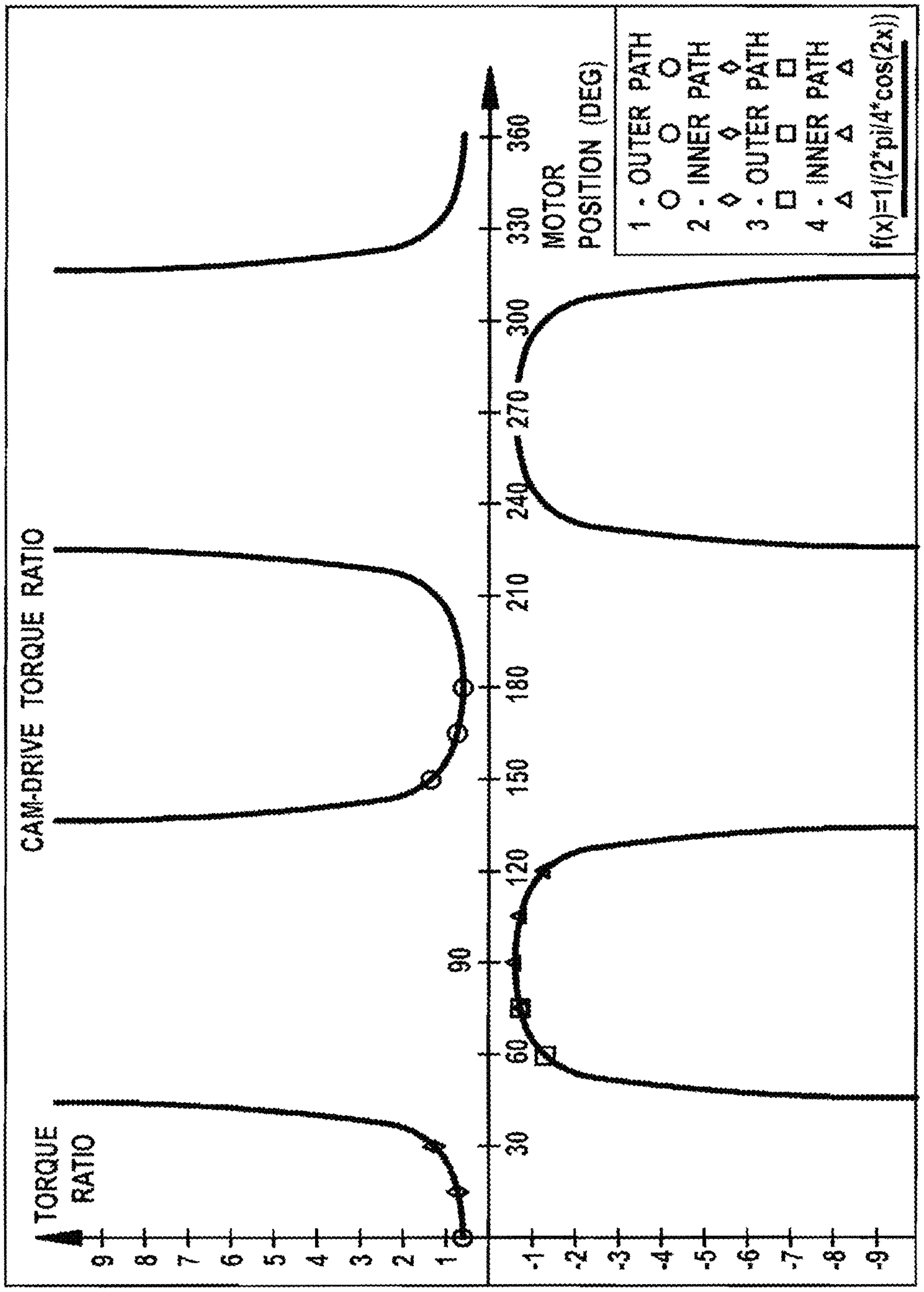
FIG. 20 is a graph of torque of the transmission of FIG. 14.

Because this formula for the Torque Ratio is different from the earlier formula, there are two formulas for computing the Torque Ratio. The first formula requires taking measurements of $L_f$, $L_c$, $A_f$ and $A_c$ at the desired locations on the cam, since these values change all along the cam profiles. The second formula, however, can be calculated for all values of θ. Both methods are plotted in FIG. 20, which shows agreement between the two formulas.

The minimum torque applied to the spindle 126 equals 0.64 times (or sixty-four percent of) the motor torque. This minimum torque occurs at the midpoint of the spindle travel, when its velocity is greatest. The torque increases exponentially at the ends of the spindle travel, as the spindle velocity approaches zero. Oscillating twice per motor revolution causes the peak velocity to increase, but causes the minimum Torque Ratio to decrease, compared to oscillating only once per motor revolution at the same motor speed.

Figure 22:
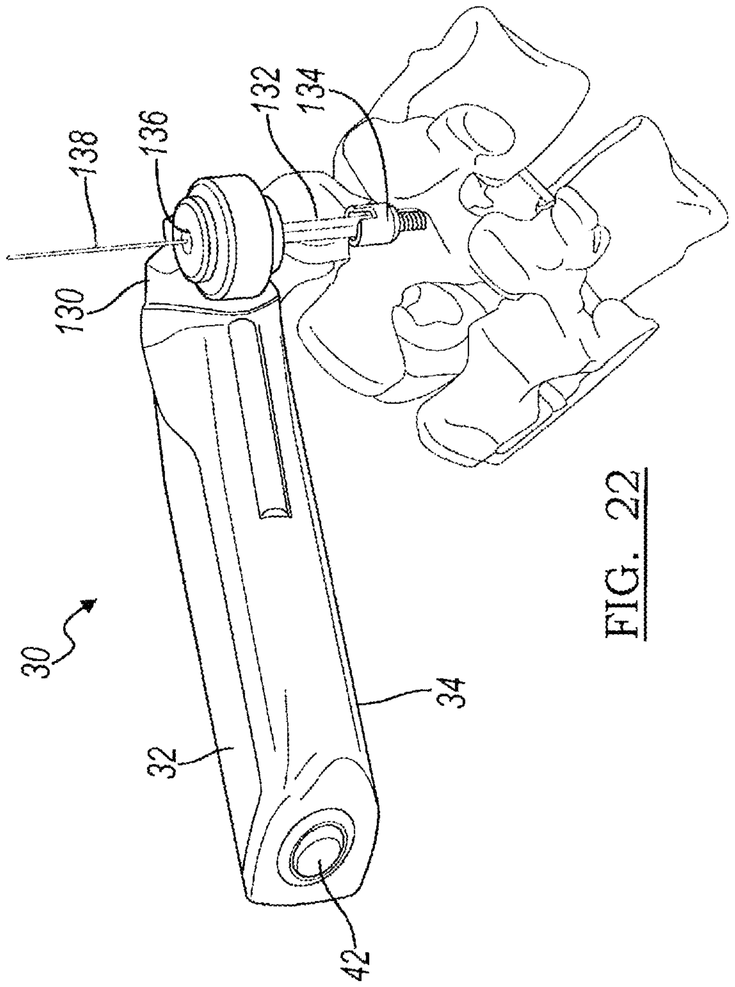
FIG. 22 is another perspective view of the tool assembly of FIG. 21 illustrated in operation.
Figure 21:
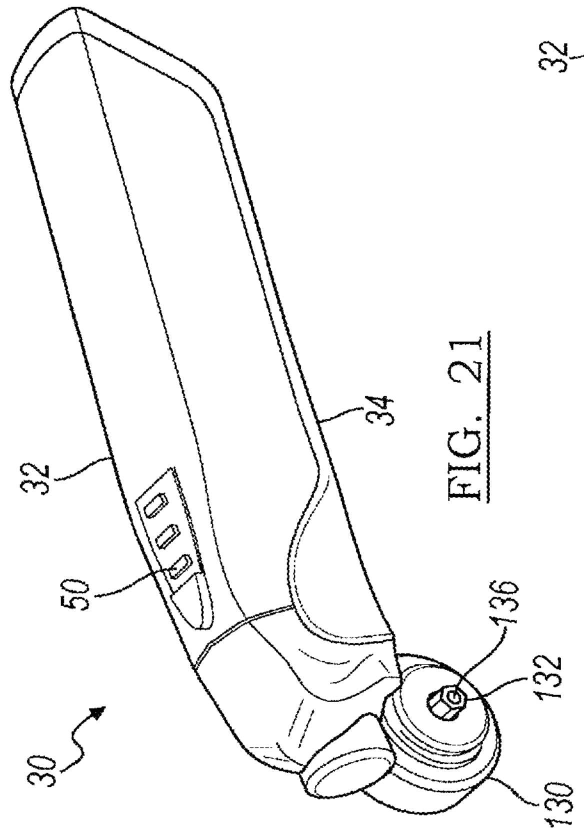
FIG. 21 is a perspective view of the tool assembly of FIG. 1, illustrated with an interchangeable drive mechanism according to another embodiment.
Figure 23:
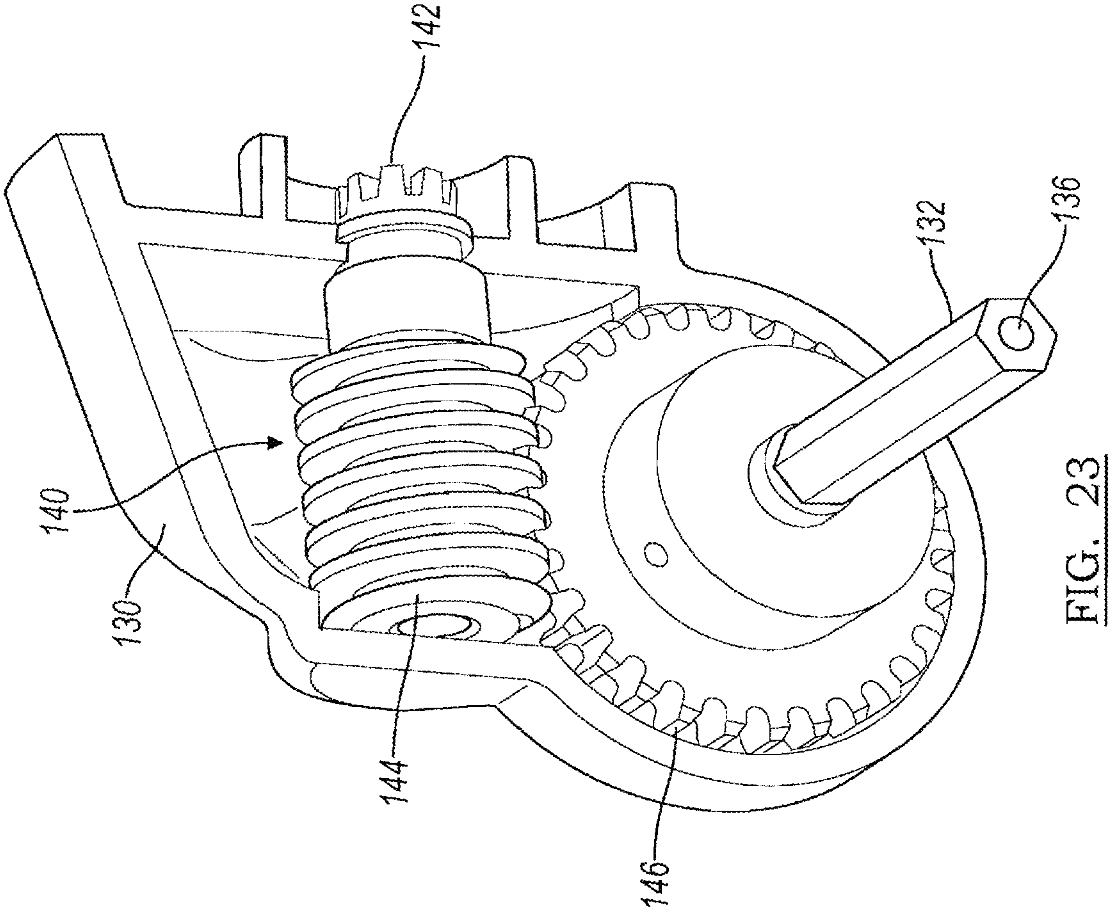
FIG. 23 is an enlarged fragmentary perspective view of a transmission of the drive mechanism of FIG. 21.

FIGS. 21 and 22 illustrate the tool assembly 30 with another front housing portion 130 interchangeably attached to the housing. The front housing portion 130 includes an output driver head 132 for driving pedicle screws 134 into a spine as illustrated in FIG. 22. An aperture 136 may extend through the front housing portion 130 for receipt of a wire guide 138 that may be utilized for alignment of the screw 134. FIG. 23 illustrates a transmission 140 with a first coupling configuration 142 for engagement with one driven by the motor 52 in the housing 32. The coupling configuration 142 drives a worm gear 144, which drives a reduction gear 146, and consequently, the drive head 132.

Figure 3:
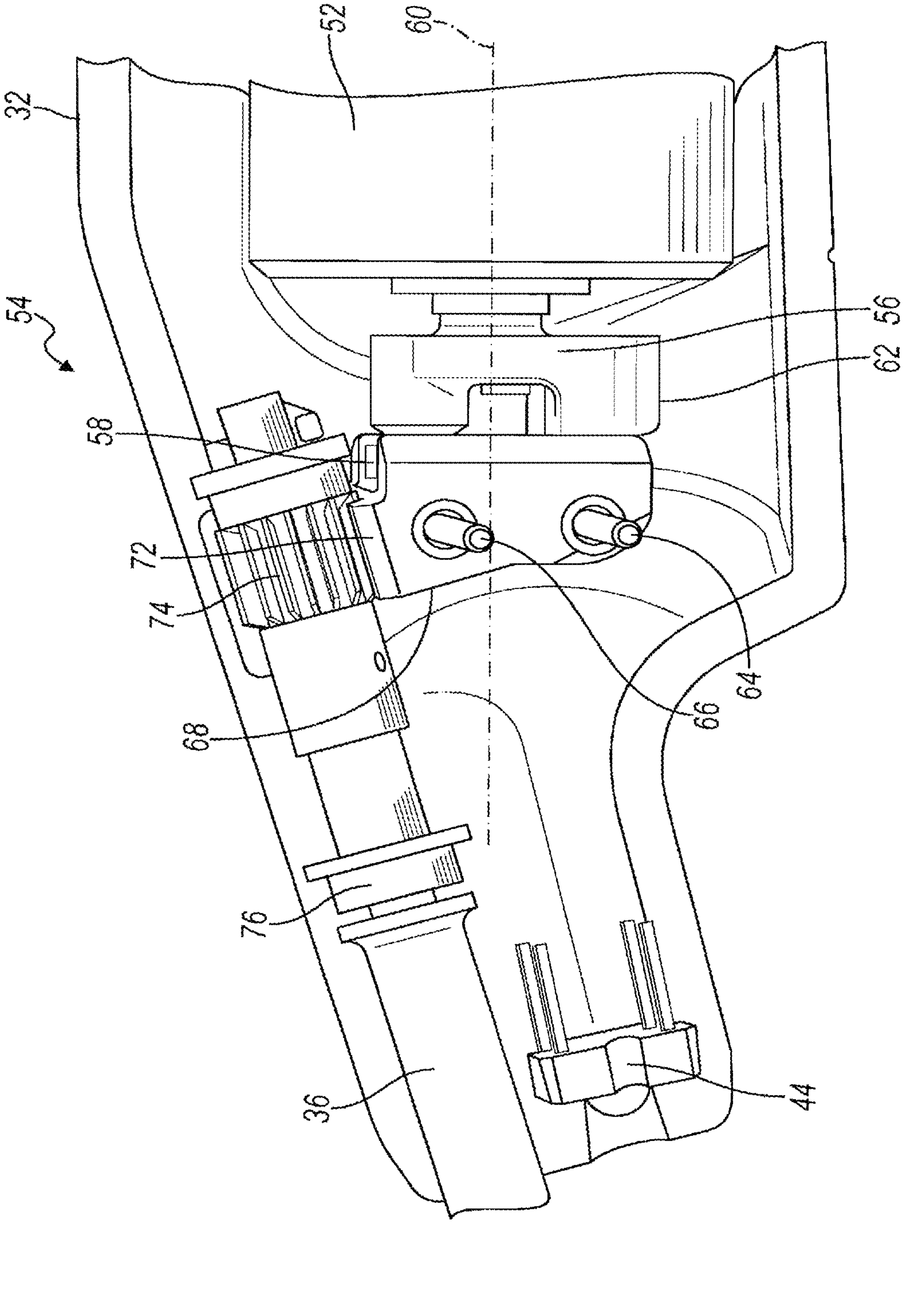
FIG. 3 is an enlarged fragmentary perspective view of a transmission of the tool assembly of FIG. 1.
Figure 5:
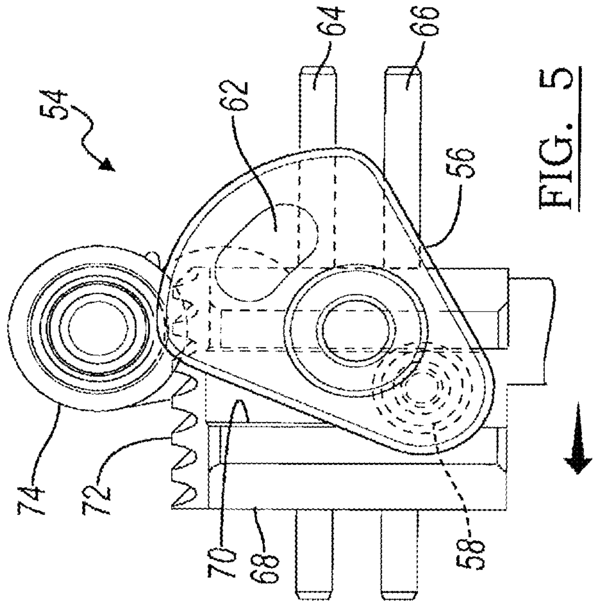
FIG. 5 is another axial schematic view of the transmission of FIG. 3, illustrating a second position.

FIG. 24 provides various example values for the transmissions of FIGS. 3 and 14 for various motor speeds to illustrate the versatility of the transmissions.

While various embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A bone, cartilage, and disk removal tool assembly comprising:
- a housing;
- a motor mounted in the housing;
- a cam mechanism having a plurality of cam profiles, wherein the motor is configured to rotate the cam mechanism;
- a follower mechanism mounted for rotation in the housing, the follower mechanism including a plurality of follower profiles, each follower profile configured to engage one of the plurality of cam profiles; and
- a spindle mounted to the housing in engagement with the follower mechanism for providing a rotary oscillating cutting operation,
- wherein the follower profiles prevent over-rotation of the spindle.

2. The bone, cartilage, and disk removal tool assembly of claim 1, wherein each of the plurality of cam profiles engages one of the plurality of follower profiles upon at least two contact points.

3. The bone, cartilage, and disk removal tool assembly of claim 1, wherein the plurality of cams profiles includes four cam profiles.

4. The bone, cartilage, and disk removal tool assembly of claim 2, wherein the plurality of follower profiles further includes four follower profiles.

5. The bone, cartilage, and disk removal tool assembly of claim 1, wherein a peak angular acceleration of the spindle is less than nine million radians per second squared.

6. The bone, cartilage, and disk removal tool assembly of claim 5, wherein angular jerk of the spindle is less than twenty-five billion radians per second cubed.

7. A bone, cartilage, and disk removal tool assembly comprising:
- a housing;
- a motor mounted in the housing;
- a spindle mounted for rotation to the housing; and
- a cam and follower mechanism operably driven by the motor and connected to the spindle to oscillate the spindle for providing a rotary oscillating cutting operation,
- wherein a plurality of follower profiles of the follower mechanism prevent over-rotation of the spindle.

8. The bone, cartilage, and disk removal tool assembly of claim 7, wherein the cam and follower mechanism further includes:
- a plurality of cams supported in the housing and driven for rotation by the motor;
- the plurality of followers mounted for rotation to the housing with the spindle, in engagement with the plurality of cams so that rotation of the plurality of cams oscillates the plurality of followers.

9. The bone, cartilage, and disk removal tool assembly of claim 7, wherein oscillations per minute of the spindle is at least double rotations per minute of the motor.

10. The bone, cartilage, and disk removal tool assembly of claim 7, wherein maximum angular velocity of said spindle is provided at the mid-point of said oscillating motion.

11. The bone, cartilage, and disk removal tool assembly of claim 7, wherein said rotary oscillating motion is at least ninety degrees of included angular displacement.

12. The bone, cartilage, and disk removal tool assembly of claim 11, wherein said rotary oscillating motion is less than one hundred and forty five degrees of included angular displacement.

13. The bone, cartilage, and disk removal tool assembly of claim 7, wherein said rotary oscillating motion is adjustable between at least ninety degrees of included angular motion and less than one hundred and forty five degrees of included angular displacement.

14. The bone, cartilage, and disk removal tool assembly of claim 7, wherein said housing includes at least one light therein, said at least one light having a beam directed at a distal end of said spindle.

15. The bone, cartilage, and disk removal tool assembly of claim 14, wherein said at least one light is a light emitting diode.

* * * * *